(12) United States Patent
Petrak et al.

(10) Patent No.: US 10,406,263 B2
(45) Date of Patent: Sep. 10, 2019

(54) ANTIMICROBIAL ARTICLES PRODUCED BY ADDITIVE MANUFACTURING

(71) Applicant: ORTHOPAEDIC INNOVATION CENTRE INC., Winnipeg, Manitoba (CA)

(72) Inventors: Martin Petrak, Winnipeg (CA); Luke M. B. Rodgers, Chaska, MN (US)

(73) Assignee: Orthopaedic Innovation Centre Inc., Winnipeg, Manitoba (CA)

( * ) Notice: Subject to any disclaimer, the term of this patent is extended or adjusted under 35 U.S.C. 154(b) by 0 days.

(21) Appl. No.: 15/127,916

(22) PCT Filed: Mar. 20, 2015

(86) PCT No.: PCT/CA2015/050211
§ 371 (c)(1),
(2) Date: Sep. 21, 2016

(87) PCT Pub. No.: WO2015/143553
PCT Pub. Date: Oct. 1, 2015

(65) Prior Publication Data
US 2017/0095596 A1 Apr. 6, 2017

Related U.S. Application Data

(60) Provisional application No. 61/969,945, filed on Mar. 25, 2014.

(51) Int. Cl.
| | |
|---|---|
| *A61K 31/7036* | (2006.01) |
| *A61K 47/34* | (2017.01) |
| *A61K 9/00* | (2006.01) |
| *A61P 31/00* | (2006.01) |
| *A61L 27/54* | (2006.01) |
| *A61K 38/14* | (2006.01) |

(Continued)

(52) U.S. Cl.
CPC .......... *A61L 27/54* (2013.01); *A61C 13/0018* (2013.01); *A61C 13/0019* (2013.01); *A61K 9/0024* (2013.01); *A61K 31/7036* (2013.01); *A61K 38/14* (2013.01); *A61K 47/32* (2013.01); *A61K 47/34* (2013.01); *A61K 47/38* (2013.01); *A61L 27/14* (2013.01); *A61L 27/18* (2013.01); *A61L 27/34* (2013.01); *A61N 1/00* (2013.01); *B29C 35/0805* (2013.01); *B29C 35/0866* (2013.01); *B29C 64/153* (2017.08); *B33Y 10/00* (2014.12); *B33Y 70/00* (2014.12); *B33Y 80/00* (2014.12); *A61B 2017/00526* (2013.01); *A61B 2017/00889* (2013.01); *A61F 2002/3097* (2013.01); *A61F 2002/30968* (2013.01); *A61F 2002/30985* (2013.01); *A61F 2240/001* (2013.01); *A61L 2300/102* (2013.01); *A61L 2300/404* (2013.01); *A61L 2300/406* (2013.01); *A61L 2430/02* (2013.01); *A61L 2430/12* (2013.01); *A61L 2430/24* (2013.01); *A61M 5/14276* (2013.01); *A61M 2205/0205* (2013.01); *A61M 2207/00* (2013.01); *B29C 2035/0838* (2013.01); *B29C 2035/0877* (2013.01); *B29K 2067/046* (2013.01); *B29K 2105/251* (2013.01); *B29K 2995/0037* (2013.01); *B29L 2031/7532* (2013.01)

(58) Field of Classification Search
None
See application file for complete search history.

(56) References Cited

U.S. PATENT DOCUMENTS

| | | | | |
|---|---|---|---|---|
| 5,508,060 A | * | 4/1996 | Perman ................ | A61K 9/1647 |
| | | | | 427/2.14 |
| 5,869,170 A | | 2/1999 | Cima et al. | |

(Continued)

FOREIGN PATENT DOCUMENTS

| | | |
|---|---|---|
| WO | 00/21470 A1 | 4/2000 |
| WO | 03/034314 A1 | 4/2003 |
| WO | 2010/019463 A1 | 2/2010 |
| WO | 2014/075185 A1 | 5/2014 |

OTHER PUBLICATIONS

Merriam-Webster Dictionary, obtained online: https://www.merriam-webster.com/dictionary/blend, downloaded on Jan. 4, 2018, pp. 1-15.*
Notification Concerning Transmittal of International Preliminary Report on Patentability dated Oct. 6, 2016 with attached International Preliminary Report on Patentability and Written Opinion received in International Application No. PCT/CA2015/050211.
Search Report and Written Opinion received in International Application No. PCT/CA2015/050211 dated Jun. 15, 2015.

*Primary Examiner* — Abigail Vanhorn
(74) *Attorney, Agent, or Firm* — Gowling WLG (Canada) LLP

(57) ABSTRACT

An antibiotic-eluting article for implantation into a mammalian subject, produced by an additive manufacturing process wherein a polymeric material is concurrently deposited with a selected antibiotic. The additive manufacturing process may be a selective laser sintering process or a selective laser melting process or a selective heat sintering process or an electron beam melting process. The antibiotic-eluting article may be temporary or permanent orthopedic skeletal component, an orthopedic articulating joint replacement component, and/or an external hard-shell casing for an implantable device. One or more bone-growth-promoting compositions may be concurrently deposited with the polymeric material. The implantable device may be a cardiac pacemaker, a spinal cord stimulator, a neurostimulation system, an intrathecal drug pump for delivery of medicants into the spinal fluid, and infusion pump for delivery of chemotherapeutics and/or anti-spasmodics, an insulin pump, an osmotic pump, and a heparin pump.

9 Claims, No Drawings

(51) Int. Cl.
| | |
|---|---|
| *A61K 47/32* | (2006.01) |
| *A61K 47/38* | (2006.01) |
| *A61L 27/14* | (2006.01) |
| *A61L 27/34* | (2006.01) |
| *A61C 13/00* | (2006.01) |
| *B33Y 10/00* | (2015.01) |
| *B33Y 70/00* | (2015.01) |
| *B33Y 80/00* | (2015.01) |
| *A61L 27/18* | (2006.01) |
| *A61N 1/00* | (2006.01) |
| *B29C 35/08* | (2006.01) |
| *B29C 64/153* | (2017.01) |
| *A61M 5/142* | (2006.01) |
| *A61B 17/00* | (2006.01) |
| *A61F 2/30* | (2006.01) |
| *B29K 67/00* | (2006.01) |
| *B29K 105/00* | (2006.01) |
| *B29L 31/00* | (2006.01) |

(56) References Cited

U.S. PATENT DOCUMENTS

| | | | |
|---|---|---|---|
| 5,869,710 A | 2/1999 | Papenfuhs | |
| 6,454,811 B1* | 9/2002 | Sherwood | A61F 2/28 623/23.72 |
| 2005/0098915 A1* | 5/2005 | Long | A61F 2/4644 264/109 |
| 2006/0228391 A1* | 10/2006 | Seyedin | A61K 31/727 424/422 |
| 2009/0019765 A1* | 1/2009 | Kosinski | C05G 1/00 47/64 |
| 2010/0063175 A1* | 3/2010 | Ginty | A61L 27/26 523/113 |
| 2010/0260703 A1* | 10/2010 | Yankelson | A61L 27/18 424/78.38 |
| 2011/0319492 A1* | 12/2011 | Luber | A61K 9/0056 514/570 |

* cited by examiner

ANTIMICROBIAL ARTICLES PRODUCED BY ADDITIVE MANUFACTURING

TECHNICAL FIELD

Various embodiments disclosed herein generally relate to implantable medical devices. More specifically, this disclosure pertains to implantable medical devices provided with antimicrobial properties throughout their structures and on their surfaces.

BACKGROUND

Numerous types of medical devices have been developed for implantation into patients' bodies. For example, it has become common practice for dentists to provide their patients with custom dental prosthesis and/or implants to replace non-functional or missing teeth. The replacement prosthesis and/or implants can be individually designed and manufactured for precise installation into specific pre-identified sites. It has become routine for patients with abnormal or irregular rates of heart contractions, to have pacemaker devices installed under their skin in the chest area or alternatively, in their abdomens. Patients with debilitating degenerative diseases affecting their joints and/or skeletal elements are now able to have a large measure of their quality of life restored by replacement of the afflicted structures with man-made artificial implants such as replacement hip components, knee joint components, shoulder components, and the like. Patients who've suffered extreme trauma resulting in severely fractured bones are often provided with fracture fixation plates, fixtures, pins, nails, intramedullary rods, and the like to hold fractured bone segments together during the healing process and/or to replace destroyed or missing skeletal segments. However, all of these types of implantable devices expose the patients to risk of post-installation infection along and/or about the outer surfaces of the devices serving as colonization sites. Particularly problematic is the establishment of infectious biofilms on the surfaces of implanted devices. More severe cases of infection often result in microbial penetration into the inner structural components of the implants requiring their removal and replacement.

Numerous strategies have been employed in attempts to prevent post-installation infections occurring on and about the surfaces the implanted medical devices. For example, flexible resilient silicone-based coatings with antimicrobial and/or anti-fungal additives have been developed for encasing the outer surfaces of medical implants at the time of implant manufacture. Such coatings are typically produced by first, dissolving a suitable silicone exemplified by methyltri-methoxy silanes, methyl tri-acetoxy silanes, tetratchlorosilanes, vinyl trimetho-ryl silanes, gamma-ureidopropyltrimethoxy silanes, and the like, in a suitable solvent exemplified by toluenes, hexanes, xylenes, tetrahydrofurans, cyclohexanones, and the like. Second, dissolving an antimicrobial compound and/or an anti-fungal compound in a suitable solvent exemplified by n-methylpyrrolidinone, alkylesters of $C_{1-12}$ carboxylic acids, and the like. Third, mixing together the silane solution and the antimicrobial and/or anti-fungal solution. Four, immersing medical implants into the mixed solutions followed by removal and air-drying of the encased implants, then baking at about 90° C. for up to one hour to set the coating and to completely evaporate the solvents. Such antibiotic-encased implants are purported to release the antimicrobial and/or anti-fungal compounds upon contact of the medical implant with tissues after implantation.

Another common approach has been to incorporate antimicrobial compounds and/or drugs into implants comprising polymeric materials, during their manufacture so that the antimicrobial compounds are eluted from the implants into the surrounding. These types of implants are generally referred to as drug-eluting implants. Some such implants are manufactured by dissolving the antimicrobial compounds into one or more solvents used for solubilising selected polymeric materials. The solubilised polymeric materials and antimicrobial compounds are mixed together and then poured or dispensed into forms wherein they solidify, and then are finished into the final implant. Other strategies involve first preparing an implant, then producing one or more recesses and/or crevices in selected locations on the outer surface, and then filling with recesses and/or crevices with a drug delivery matrix that this allowed to at least semi-harden. The drugs are then eluted from the matrix over a period of time. In some implant combinations, for example a "ball" and "socket" combination for a complete hip replacement or a total knee replacement package comprising a femoral component, a tibial tray, a tibial insert, and a patellar component, the drug delivery matrix may be incorporated into weight-bearing surfaces of one or more components so that the drugs are released by frictional forces created when two or more implant components rub against each other during their normal articulating functions. Other implant drug-eluting strategies have reservoirs cast into the implants' interior structure. The reservoirs are filled with drug solutions prior to installation of an implant into a patient. Some implants are configured to communicate and cooperate with external reservoirs containing drug solutions that are externally pumped into and/or about the implants on prophylactic schedules or alternatively, when an infection is detected. It is general practise to use antibiotic-loaded cements exemplified by PROSTALAC® (PROSTALAC is a registered trademark of Depuy Orthopaedic Inc., Warsaw, Ind., USA) and SIMPLEX® (SIMPLEX is a registered trademark of Howmedica Osteonics Corp., Mahwah, N.J., USA) for installation of orthopaedic implants. While these cements have considerable value for minimizing the occurrence of post-operative infections immediately after installation of orthopaedic implants, their long-term benefits are limited because the antibiotics tend to rapidly dissipate from the surfaces of the cements upon exposure to mammalian tissues.

There still remain numerous infection-susceptibility related problems with the implants commonly available and in general use. There are concerns that the efficacies of some antimicrobial compounds and/or drugs are altered or compromised by the solvents which are used for their dissolution and/or by solvents used for dissolution of polymeric materials used for casting implants. Furthermore, it is known that the efficacies of drug-eluting implants increasingly diminish over time and are limited by drug "loading" limitations by the implant manufacturing processes. Implants provided with drug-loaded recesses/crevices may provide protection from infections about the crevice sites for a period of time, but are quite susceptible to microbial colonization and biofilm formation on their surface areas at locations removed from the recesses/crevices. Compounding these problems, are the surgical challenges of removing the infected implants, abrading surrounding infected skeletal structures, excising surrounding infected tissues, and installing replacement implants.

SUMMARY

The present disclosure pertains to implantable antimicrobial medical devices having antimicrobial compounds evenly sequestered throughout their structural matrices and distributed across their surfaces. The antimicrobial compounds may be eluted from the surfaces and from within the structural matrices after implantation of the medical devices into a mammalian subject. The present disclosure also pertains to methods for producing implantable medical devices comprising elutable antimicrobial compounds sequestered within their structural matrices and distributed across their surfaces.

DETAILED DESCRIPTION

The present disclosure pertains to methods for producing implantable antibiotic-eluting polymeric medical devices having antimicrobial compounds and/or bactericidal compounds homogenously distributed and sequestered throughout their structural matrix and across their surfaces. The present disclosure also pertains to implantable antibiotic-sequestering and eluting medical devices produced by the exemplary methods disclosed herein.

The exemplary methods of the present disclosure are particularly useful for producing substantially rigid articles that are suitable for surgical implantation into mammalian bodies, for example humans, primates, livestock, ruminants, equines, canines, felines, and the like.

The exemplary methods are also useful for producing external hard-shell casings for implantable devices such as cardiac pacemakers, spinal cord stimulators, neurostimulation systems, intrathecal drug pumps for delivery of medicants into the spinal fluid, infusion pumps for delivery of chemotherapeutics and/or anti-spasmodics, insulin pumps, osmotic pumps, heparin pumps, and the like. The exemplary methods are also useful for producing dental prosthesis, dental implants comprising one or more replacement tooth components, and the like. The exemplary methods are also useful for producing transcutaneous skin surface treatment devices exemplified by devices for providing transcutaneous electrical nerve stimulation and by devices for providing long-term percutaneous access. The exemplary methods are also useful for producing wound treatment surface devices exemplified by staples and sutures, and the like. The exemplary methods are particularly useful for producing three-dimensional intricate orthopaedic skeletal components including but not limited to articulating joint replacements, hip joint spacers, knee joint spacers, shoulder joint spacers, and the like. The three-dimensional intricate orthopaedic skeletal components may be temporary structures or alternatively, permanent structures.

The exemplary methods generally incorporate into manufacturing processes using additive manufacturing technologies, the concurrent deposition of one or more antimicrobial and/or biocidal compositions with the base feedstock materials to form the three-dimensional physical structures comprising the implantable antimicrobial articles of the present disclosure. The articles may be formed into solid and dense non-porous three-dimensional structures. Alternatively, the structures may be formed into heterogenous three-dimensional structures comprising solid regions and porous regions. Alternatively, the structures may comprise inner cores having heterogenous three-dimensional structures that are overlaid with outer coverings comprising one or more solid dense layers. One or more selected antimicrobial compositions may be incorporated into the inner cores and/or into the outer coverings. Alternatively, the structures may comprise inner cores comprising a first heterogenous three dimensional structure with a first degree of porosity, overlaid with one or more layers of a second heterogenous three dimensional structure with a second degree of porosity. One or more selected antibiotic compositions may be incorporated into the inner cores and/or into the outer layers. If so desired, the articles can be formed having more than three zones of porosity ranging from the inner cores to the outer surfaces.

Suitable additive manufacturing technologies include molten polymer deposition exemplified by selective laser sintering, selective laser melting, selective heat sintering, electron beam melting, and the like. One or more antibiotic compositions are concurrently deposited with the polymeric materials resulting in sequestration of the antibiotic compositions within and about the matrix formed by the polymeric materials. The antibiotic compositions are deposited at rates that will provide in the articles of the present disclosure, from about 0.01% w/w to about 25% w/w of the antibiotic active ingredient by weight of the total weight of an antimicrobial article. For example, about 0.01% w/w, about 0.05% w/w, about 0.1% w/w, about 0.2% w/w, about 0.3% w/w, about 0.4% w/w, about 0.5% w/w, about 0.75% w/w, about 1.0% w/w, about 1.25% w/w, about 1.5% w/w, about 1.75% w/w, about 2.0% w/w, about 2.25% w/w, about 2.5% w/w, about 2.75% w/w, about 3.0% w/w, about 3.25% w/w, about 3.5% w/w, about 3.75% w/w, about 4.0% w/w, about 4.25% w/w, about 4.5% w/w, about 4.75% w/w, about 5.0% w/w, about 5.25% w/w, about 5.5% w/w, about 5.75% w/w, about 6.0% w/w, about 7.0% w/w, about 8.0% w/w, about 9.0% w/w, about 10.0% w/w, about 15.0% w/w, about 20.0% w/w, about 25.0% w/w, and therebetween.

The term "antimicrobial" as used herein means antibiotic, antiseptic, disinfectant. Classes of antibiotic compositions that may be useful for in the methods of the present disclosure for producing antimicrobial implantable medical devices include aminoglycosides exemplified by tobramycin, gentamicin, neomycin, streptomycin, and the like; azoles exemplified by fluconazole, itraconazole, and the like; β-lactam antibiotics exemplified by penams, cephems, carbapenems, monobactams, β-lactamase inhibitors, and the like; cephalosporins exemplified by cefacetrile, cefadroxyl, cephalexin, cephazolin, cefproxil, cefbuperazone, and the like; chloramphenicol; clindamycin; fusidic acid; glycopeptides exemplified by vancomycin, teicoplanin, ramoplanin, and the like; macrolides exemplified by azithromycin, clarithromycin, dirithromysin, erythromycin, spiramycin, tylosin, and the like; metronidazole; mupirocin; penicillins exemplified by benzylpenicillin, procaine benzylpenicillin, benzathine benzylpenicillin, phenoxymethylpenicillin, and the like; polyenes exemplified by amphotericin B, nystatin, natamycin, and the like; quinolones exemplified by ciprofloxacin, ofloxacin, danofloxacin, and the like; rifamycins exemplified by rifampicin, rifabutin, rifapentine, rifaximin, and the like; sufonamides exemplified by sulfacetamine, sulfadoxine, and the like; tetracyclines exemplified by doxycycline, minocycline, tigecycline, and the like; and trimethoprim, among others. It is expected that tobramycin and/or gentamicin and/or neomycin and/or vancomycin are particularly suitable for concurrent deposition with polymeric materials for additive manufacturing of the antimicrobial medical devices of the present disclosure.

Various thermoplastic polymers and/or free radical polymers and/or cross-linked polymers may be used for concurrent deposition with antibiotic compositions to produce the antimicrobial articles disclosed herein. For example poly (methyl methacrylates), acrylonitrile butadiene styrenes, polycarbonates, blends of acrylonitrile butadiene styrene(s) and polycarbonate(s), polyether ether ketones, polyethylenes, polyamides, polylactic acids, polyphenylsulfones, polystyrenes, nylon particularly nylon 12, among others. Also useful are methylmethacrylates, polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, block copolymers, multi-block co-polymers, multi-block co-polymers with polyethylene glycol (PEG), polyols, terpolymers and mixtures thereof. Also useful is incorporation of glass fibres during deposition of selected polymers and antibiotic compositions.

If so desired for manufacture of the three-dimensional intricate orthopaedic skeletal components disclosed herein, one or more bone-growth-promoting compositions may be deposited concurrently with the polymeric materials and the antibiotic compositions resulting in sequestration of the antibiotic compositions and bone-growth-promoting compositions within and about the matrix formed by the polymeric materials. Suitable bone-growth-promoting compositions are exemplified by hyaluronic acid, β-TCP compositions, SOST (sclerostin) antagonists for modulating the Wnt signaling pathway, Wise antagonists for modulating the Wnt signaling pathway, LRP antagonists for modulating the Wnt signaling pathway, (3-(((4-tert-butyl-benzyl)-(pyridine-3-sulfonyl)-amino)-methyl)-phenoxy)-acetic-acid and its analogs, 7-[(4-butyl-benzyl)-methanesulfonyl-amino]-heptanoic acid and its analogs, 7-{[2-(3,5-dichloro-phenoxyl)-ethyl]-methanesulfonyl-amino}-heptanoic acid and its analogs, 3-benzothiepin derivatives, and the like.

Granular materials binding processes exemplified by selective laser sintering, selective laser liquefying, selective heat sintering and electron beam liquefying (all referred to herein as "SLS"), comprise selective fusing of print media in a granular bed. In this type of method, a high power laser is used to fuse small particles of plastic, metal, ceramic, or glass powders into a mass that has a desired three-dimensional shape. The laser selectively fuses powdered material by scanning cross-sections generated from a 3-D digital description of the part (for example from a CAD file or scan data) on the surface of a powder bed. After each cross-section is scanned, the powder bed is lowered by one layer thickness, a new layer of material is applied on top, and the process is repeated until the part is completed. Because finished part density depends on peak laser power rather than laser duration, a SLS machine typically uses a pulsed laser. A suitable SLS machine preheats the bulk powder material in the powder bed somewhat below its melting point, to make it easier for the laser to raise the temperature of the selected regions the rest of the way to the melting point.

Accordingly, the exemplary implantable polymeric antimicrobial devices disclosed herein may also be produced by SLS 3D printing machines by providing powdered blends of one or more selected granular polymers with one or more selected antibiotic compositions and/or one or more bone-growth-promoting composition. Suitable SLS 3D printing machines are manufactured by EOS GmbH (Munich, Fed. Rep. Germany) and are available in North America from EOS of North America Inc. (Novi, Mich., USA). Suitable EOS SLS 3D printing machines include their FORMIGA® P 110, EOSINT® P 395, EOSINT® P 760, and EOSINT® P 800 equipment (FORMIGA and EOSINT are registered trademarks of EOS GmbH Electro Optical Systems Co., Krailling, Fed. Rep. Germany). Suitable SLS 3D printing machines are also manufactured and supplied by 3D Systems Inc. (Rock Hill, S.C., USA) and are exemplified by their SPRO® line of equipment (SPRO is a registered trademark of 3D Systems Inc.). Suitable electron beam melting (also referred to as EBM) 3D printing machines are manufactured by Arcam AB (Molndal, Sweden) and are available in North America from their office in Chicago, Ill. Suitable Arcam EBM 3D printing machines include their Q10 and A2 equipment.

Suitable exemplary powdered antibiotic/polymer compositions for SLS 3D printing may comprise granules of one or more of poly(methyl methacrylates), acrylonitrile butadiene styrenes, polycarbonates, blends of acrylonitrile butadiene styrene(s) and polycarbonate(s), polyether ether ketones, polyethylenes, polyamides, polylactic acids, polyphenylsulfones, polystyrenes, nylon particularly nylon 12, among others. Also useful are methylmethacrylates, polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, block copolymers, multi-block co-polymers, multi-block co-polymers with polyethylene glycol (PEG), polyols, terpolymers and mixtures thereof.

Suitable powdered antibiotic/polymer compositions for SLS 3D printing may comprise one or more of aminoglycosides exemplified by tobramycin, gentamicin, neomycin, streptomycin, and the like; azoles exemplified by fluconazole, itraconazole, and the like; β-lactam antibiotics exemplified by penams, cephems, carbapenems, monobactams, β-lactamase inhibitors, and the like; cephalosporins exemplified by cefacetrile, cefadroxil, cephalexin, cephazolin, cefproxil, cefbuperazone, and the like; chloramphenicol; clindamycin; fusidic acid; glycopeptides exemplified by vancomycin, teicoplanin, ramoplanin, and the like; macrolides exemplified by azithromycin, clarithromycin, dirithromysin, erythromycin, spiramycin, tylosin, and the like; metronidazole; mupirocin; penicillins exemplified by benzylpenicillin, procaine benzylpenicillin, benzathine benzylpenicillin, phenoxymethylpenicillin, and the like; polyenes exemplified by amphotericin B, nystatin, natamycin, and the like; quinolones exemplified by ciprofloxacin, ofloxacin, danofloxacin, and the like; rifamycins exemplified by rifampicin, rifabutin, rifapentine, rifaximin, and the like; sufonamides exemplified by sulfacetamine, sulfadoxine, and the like; tetracyclines exemplified by doxycycline, minocycline, tigecycline, and the like; and trimethoprim, among others. The antibiotic content of exemplary powdered antibiotic/polymer compositions for SLS 3D printing may comprise about 0.01% w/w, about 0.05% w/w, about 0.1% w/w, about 0.2% w/w, about 0.3% w/w, about 0.4% w/w, about 0.5% w/w, about 0.75% w/w, about 1.0% w/w, about 1.25% w/w, about 1.5% w/w, about 1.75% w/w, about 2.0% w/w, about 2.25% w/w, about 2.5% w/w, about 2.75% w/w, about 3.0% w/w, about 3.25% w/w, about 3.5% w/w, about 3.75% w/w, about 4.0% w/w, about 4.25% w/w, about 4.5% w/w, about 4.75% w/w, about 5.0% w/w, about 5.25% w/w, about 5.5% w/w, about 5.75% w/w, about 6.0% w/w, about 7.0% w/w, about 8.0% w/w, about 9.0% w/w, about 10.0% w/w, about 15.0% w/w, about 20.0% w/w, about 25.0% w/w, and therebetween.

Suitable powdered antibiotic/polymer compositions for SLS 3D printing may comprise one or more of hyaluronic acid, β-TCP compositions, SOST (sclerostin) antagonists for modulating the Wnt signaling pathway, Wise antagonists for modulating the Wnt signaling pathway, LRP antagonists for modulating the Wnt signaling pathway, (3-(((4-tert-butyl-benzyl)-(pyridine-3-sulfonyl)-amino)-methyl)-phenoxy)-acetic-acid and its analogs, 7-[(4-butyl-benzyl)-methanesulfonyl-amino]-heptanoic acid and its analogs, 7-{[2-(3,5-dichloro-phenoxyl)-ethyl]-methanesulfonyl-amino}-heptanoic acid and its analogs, 3-benzothiepin derivatives, and the like. The bone-growth-promoting composition content of exemplary powdered antibiotic/polymer compositions for SLS 3D printing may comprise about 0.01% w/w, about 0.05% w/w, about 0.1% w/w, about 0.2% w/w, about 0.3% w/w, about 0.4% w/w, about 0.5% w/w, about 0.75% w/w, about 1.0% w/w, about 1.25% w/w, about 1.5% w/w, about 1.75% w/w, about 2.0% w/w, about 2.25% w/w, about 2.5% w/w, about 2.75% w/w, about 3.0% w/w, about 3.25% w/w, about 3.5% w/w, about 3.75% w/w, about 4.0% w/w, about 4.25% w/w, about 4.5% w/w, about 4.75% w/w, about 5.0% w/w, about 5.25% w/w, about 5.5% w/w, about 5.75% w/w, about 6.0% w/w, about 7.0% w/w, about 8.0% w/w, about 9.0% w/w, about 10.0% w/w, about 15.0% w/w, about 20.0% w/w, about 25.0% w/w, and therebetween.

The 3D printing methods of the present disclosure may additionally include additionally or alternatively comprise steps of concurrent deposition of a first antibiotic composition or mixture of antibiotic compositions and/or a first bone-growth-promoting composition with a selected polymeric material in several layers to form the core of a three-dimensional antimicrobial article, followed by concurrent deposition of a second first antibiotic composition or mixture of antibiotic compositions and/or a second bone-growth-promoting composition with the selected polymeric material to form the outer regions and surfaces of the antimicrobial article. The methods may additionally comprise concurrent deposition of additional layers of a third antibiotic composition or mixture of antibiotic compositions and/or a third bone-growth-promoting composition if so desired. It is optional to provide a final outer surface layer to which is added a biocidal composition exemplified by silver nanoparticles, zinc pyrithione, cationic polymeric biocides, and the like. It is optional to provide a final outer surface layer to which is added a bone-growth-promoting composition exemplified by hyaluronic acid, β-TCP compositions, 3-benzothiepin derivatives, and the like.

It is also optional to provide a final outer surface layer to which is added mixture of a biocidal composition and a bone-growth-promoting composition. The outer surface layer comprising the biocidal coating and/or the bone-growth-promoting composition may be applied by the same additive manufacturing process used to produce the core structural matrix of the three-dimensional antimicrobial article. Alternatively, the outer surface layer may be applied as a coating over the core structural matrix of the three-dimensional antimicrobial article. The outer coating may be applied by processes exemplified by dipping, spraying, soaking, infusing, powder-coating, sputter-coating, arc depositing, and the like.

The antibiotic-eluting articles of the present disclosure are exemplified by orthopaedic skeletal components, orthopaedic articulating joint replacement components, and bone spacers. Also included are temporary orthopaedic components for short-term implantation while the permanent replacement orthopaedic components are being produced. The term "short-term" as used herein means three hundred and sixty five (365) days and less. The antibiotic-eluting articles of the present disclosure are also exemplified by external hard-shell casings for implantable devices such as cardiac pacemakers, spinal cord stimulators, neurostimulation systems, intrathecal drug pumps for delivery of medicants into the spinal fluid, infusion pumps for delivery of chemotherapeutics and/or anti-spasmodics, insulin pumps, osmotic pumps, heparin pumps, and the like. The antibiotic-eluting articles of the present disclosure are also exemplified by implantable dental prosthesis, dental implants comprising one or more replacement tooth components, and the like. The antibiotic-eluting articles of the present disclosure are also exemplified by transcutaneous skin surface treatment devices for providing transcutaneous electrical nerve stimulation and by devices for providing long-term percutaneous access. The antibiotic-eluting articles of the present disclosure are also exemplified by wound treatment surface devices exemplified by staples and sutures, and the like.

EXAMPLES

Example 1

Polylactide (PLA) granules were sourced from NatureWorks LLC (Blair, Nebr., USA). Polycaprolactone (PCL) granules (CAPA™ 6500) were sourced from Plastics Systems Inc. (Lakewood, Wash., USA). Vancomycin and Gentamicin were sourced from Gold Biotechnology (St. Louis, Mo., USA). 0.28 kg of Vancomycin was dry-blended together with a 5.8 Kg batch of PLA granules to produce a PLA blend comprising about 5% Vancomycin. 0.122 kg of Vancomycin was dry-blended together with a 5.8 Kg batch of PLA granules to produce a PLA blend comprising about 2% Vancomycin. 0.125 Kg of Gentamicin was dry-blended together with a 2.5 Kg batch of PCL granules to produce a PCL blend comprising about 5% Gentamicin. A PCL blend comprising about 2% Gentamicin was prepared by dry-blending a PCL blend comprising about 5% Gentamicin with additional PCL to adjust the Gentamicin content to about 2%.

A SINTERSTATION® HiQ SLS® system (SINTERSTATION and SLS are registered trademarks of 3D Systems Inc., Valencia, Calif., USA) was used to print round discs having about diameter of about 1 inch (2.54 cm) and a thickness of about 0.125 inch (0.3175 cm) from each batch of polymer/antibiotic blends. Control discs were printed from pure PLA granules and PCL granules. About 4 inches of a polymer/antibiotic blend was placed into the machine's feed cylinders, and a powder bed was then generated by depositing powder onto the part cylinder. A warm up cycle was then used to warm both the feed cylinder and part cylinder, after which, the discs printed according to STL CAD software files loaded into 3D System's "Build Setup" Version 3.602 software. A portion of each polymer/antibiotic blend was used for SLS printing of discs for assessment of their antibiotic-eluting performance, and the remainder of the polymer/antibiotic blend was used for printing Type IV dumb-bell-shaped test specimens for tensile testing.

The system operating conditions for SLS printing of discs and Type IV dumb-bell-shaped specimens from PCL/Vancomycin blends and from PCL/Gentamicin blends were:

| | |
|---|---|
| Particle bed temperature: | 48° C. |
| Feed temperature: | ambient |
| Smart feed gain: | 1.3 |

-continued

| | |
|---|---|
| Fill laser power (W): | 49 |
| Fill scan speed (inches/sec): | 500 |
| Fill scan spacing (inches): | 0.01 |
| Outline laser power (W): | 14 |
| Outline scan speed (inches/sec): | 70 |

The system operating conditions for SLS printing of the discs from PLA/Vancomycin blends and from PLA/Gentamicin blends were:

| | |
|---|---|
| Particle bed temperature: | 75° C. |
| Feed temperature: | 40° C. |
| Smart feed gain: | 1.3 |
| Fill laser power (W): | 67 |
| Fill scan speed (inches/sec): | 500 |
| Fill scan spacing (inches): | 0.01 |
| Outline laser power (W): | 14 |
| Outline scan speed (inches/sec): | 70 |

Example 2

Selected physical properties of the antibiotic-containing plastic Type IV dumb-bell-shaped test specimens were determined following the test methods set out in ASTM D638-08 document titled "Standard Test Method for Tensile Properties of Plastics" published by ASTM International and publicly available from their website: http://www.astm.org/Standards/D638.htm. The physical properties of the SLS-printed antibiotic-containing plastic discs are listed in Tables 1-4.

TABLE 1

Physical properties of Type IV dumb-bell-shaped specimens printed with PCL/Gentamicin dry blends*.

| | Gentamicin content in PCL discs | | |
|---|---|---|---|
| Physical parameter | 0 | 2% | 5% |
| Thickness (in) | 0.134 | 0.134 ± 0.001 | 0.138 ± 0.001 |
| Modulus (lbf/in$^2$) | 53200 | 47700 ± 1700 | 314000 ± 4330 |
| 0.2% Offset yield strength (lbf/in$^2$) | 1970 | 1150 ± 67 | 1210 ± 191 |
| Ultimate strength (lbf/in$^2$) | 3090 | 1990 ± 26 | 1830 ± 13 |
| % elongation at offset yield (%) break | 407 | 4032.72 ± 0.96 | 1.23 ± 0.68 |

*data are means of three replicates ± SD

TABLE 2

Physical properties of Type IV dumb-bell-shaped specimens printed with PCL/Vancomycin dry blends.

| | Vancomycin content in PCL discs | | |
|---|---|---|---|
| Physical parameter | 0 | 2% | 5% |
| Thickness (in) | 0.134 | 0.128 ± 0.001 | 0.129 ± 0.001 |
| Modulus (lbf/in$^2$) | 53200 | 94200 ± 3720 | 65900 ± 4750 |
| 0.2% Offset yield strength (lbf/in$^2$) | 1970 | 1150 ± 67 | 1130 ± 71 |
| Ultimate strength (lbf/in$^2$) | 3090 | 1430 ± 130 | 1930 ± 167 |
| % elongation at offset yield (%) break | 407 | 1.41 ± 0.25 | 1.76 ± 0.28 |

*data are means of three replicates ± SD

TABLE 3

Physical properties of Type IV dumb-bell-shaped specimens printed with PLA/Gentamicin dry blends*.

| | Gentamicin content in PCL discs | | |
|---|---|---|---|
| Physical parameter | 0** | 2% | 5% |
| Thickness (in) | — | 0.156 ± 0.001 | 0.158 ± 0.001 |
| Modulus (lbf/in$^2$) | — | 155000 ± 5680 | 164000 ± 7010 |
| 0.2% Offset yield strength (lbf/in$^2$) | — | 919 ± 45 | 980 ± 191 |
| Ultimate strength (lbf/in$^2$) | — | 1130 ± 75 | 1170 ± 104 |
| % elongation at offset yield (%) break | — | 0.569 ± 0.2 | 0.66 ± 0.13 |

*data are means of three replicates ± SD
**the control PLA granules did not sinter well and did not hold its structure

TABLE 4

Physical properties of Type IV dumb-bell-shaped specimens printed with PLA/Vancomycin dry blends*.

| | Vancomycin content in PCL discs | | |
|---|---|---|---|
| Physical parameter | 0** | 2% | 5% |
| Thickness (in) | — | 0.152 ± 0.001 | 0.156 ± 0.001 |
| Modulus (lbf/in$^2$) | — | 161000 ± 7950 | 124000 ± 1930 |
| 0.2% Offset yield strength (lbf/in$^2$) | — | 903 ± 190 | 849 ± 111 |
| Ultimate strength (lbf/in$^2$) | — | 1090 ± 69 | 962 ± 67 |
| % elongation at offset yield (%) break | — | 0.538 ± 0.14 | 0.545 ± 0.12 |

*data are means of three replicates ± SD
**the control PLA granules did not sinter well and none of the control Type IV dumb-bell-shaped specimens held their structures Example 2

The elution of antibiotics from the discs produced in Example 1 was assessed by the inhibition of the growth of Staphylococcus aureus on the surfaces of Meuller Hinton agar contained within Petri dishes onto which test coupons placed. S. aureus cultures were grown on TSA amended with 5% sheep blood. A sufficient amount of S. aureus culture was transferred from the TSA culture plates to a 0.85% sterile saline solution to provide a uniform suspension that fell within a 0.5-2.0 McFarland turbidity standard. Aliquots of the S. aureus culture were plated onto Meuller Hinton agar in Petri dishes after which, two test coupons/dish (or alternatively, control coupons) were placed on the agar; one with its shiny side up and the other with its matte side up. The Meuller Hinton agar-containing Petri dishes were then incubated for about 72 hrs at temperatures in the range of about 35° C. to about 37° C. The zones of inhibition around each coupon were then measured and recorded (in mm). A clear zone around a test coupon indicates the inhibition of growth of *S. aureus*. The diameter of the PLA/Antibiotic blend coupons were 25 mm and 26 mm for the PCL/Antibiotic coupons. The diameters of the PLA control coupon were 25 mm and 26 mm respectively, and considered as the "0" points. If no inhibition occurred, then the value "25" was recorded and indicates that no inhibition of microbial growth occurred. The data shown in Table 5 confirm that the antibiotics were eluted from articles printed from each polymer/antibiotic blend.

TABLE 5

Elution of antibiotics from 3d-printed articles comprising PCL or PLA*.

| Polymer/antibiotic blend | Antibiotic concentration | | |
|---|---|---|---|
| | 0 | 2% | 5% |
| PCL/Gentamicin | 25 | 43.7 | 45.0 |
| PCL/Vancomycin | 25 | 42.0 | 41.7 |
| PLA/Gentamicin | 32 | 41.7 | 43.7 |
| PLA/Vancomycin | 32 | 40.3 | 43.7 |

*data are means of three replicates ± SD

The invention claimed is:

1. A dry antibiotic-containing polymeric granular powder blend consisting of:
a polymeric granular powder; and
at least about 1% w/w of at least one antibiotic powder, said dry antibiotic-containing polymeric granular powder for use by any one of a selective laser sintering machine, a selective laser liquefying machine, a selective heat sintering machine, and an electron beam liquefying machine.

2. The dry antibiotic-containing polymeric granular powder blend of claim 1, wherein the polymer is selected from a group consisting of poly(methyl methacrylates), acrylonitrile butadiene styrenes, polycarbonates, blends of acrylonitrile butadiene styrene(s) and polycarbonate(s), polyether ether ketones, polyethylenes, polyamides, polylactic acids, polyphenylsulfones, polystyrenes, nylons, methylmethacrylates, polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, block copolymers, multi-block co-polymers, multi-block co-polymers with polyethylene glycol (PEG), polyols, terpolymers, and mixtures thereof.

3. The dry antibiotic-containing polymeric granular powder blend of claim 1, wherein the polymer is selected from a group consisting of polylactic acid, polycaprolactones, nylons, and high-density polyethylene.

4. The dry antibiotic-containing polymeric granular powder blend of claim 1, wherein the antibiotic is selected from a group consisting of an aminoglycoside, an azole, a β-lactam antibiotic, a β-lactamase inhibitor, a cephalosporin, chloramphenicol, clindamycin, fusidic acid, a glycopeptide, a macrolide, metronidazole, mupirocin, a penicillin, a polyene, a quinolone, a rifamycin, a sufonamide, a tetracycline, trimethoprim, and combinations thereof.

5. The dry antibiotic-containing polymeric granular powder blend of claim 1, wherein the concentration of the at least one antibiotic is selected from a range of about 1.0% w/w to about 25.0% w/w.

6. The dry antibiotic-containing polymeric granular powder blend of claim 1, wherein the concentration of the at least one antibiotic is selected from a range of about 1.0% w/w to about 10.0% w/w.

7. The dry antibiotic-containing polymeric granular powder blend of claim 1, wherein the concentration of the at least one antibiotic is selected from a range of about 1.0% w/w to about 5.0% w/w.

8. A dry antibiotic-containing polymeric granular powder blend consisting of: a polymeric granular powder; at least about 1% w/w of at least one antibiotic powder; and a bone growth promoter selected from a group consisting of hyaluronic acid, SOST (sclerostin) antagonists for modulating the Wnt signaling pathway, Wise antagonists for modulating the Wnt signaling pathway, LRP antagonists for modulating the Wnt signaling pathway, (3-(((4-tert-butyl-benzyl)-(pyridine-3-sulfonyl)-amino)-methyl)-phenoxy)-acetic-acid and its analogs, 7-[(4-butyl-benzyl)-methanesulfonyl-amino]-heptanoic acid and its analogs, and 7-{[2-(3,5-dichloro-phenoxy)-ethyl]-methanesulfonyl-amino}-heptanoic acid and its analogs, and 3-benzothiepin derivatives; said dry antibiotic-containing polymeric granular powder for use by any one of a selective laser sintering machine, a selective laser liquefying machine, a selective heat sintering machine, and an electron beam liquefying machine.

9. The dry antibiotic-containing polymeric granular powder blend of claim 4, wherein the tetracycline is doxycycline, minocycline, or tigecycline.

* * * * *